United States Patent [19]
Lopez

[11] Patent Number: 5,810,768
[45] Date of Patent: Sep. 22, 1998

[54] MEDICAL CONNECTOR

[75] Inventor: George A. Lopez, Laguna Beach, Calif.

[73] Assignee: ICU Medical, Inc., San Clemente, Calif.

[21] Appl. No.: 480,615

[22] Filed: Jun. 7, 1995

[51] Int. Cl.⁶ .................................................. A61M 31/00
[52] U.S. Cl. ............................ 604/56; 604/83; 604/256; 604/247; 128/760
[58] Field of Search .................................. 604/28, 33, 34, 604/56, 83, 91, 249, 247, 256; 251/149–149.1, 339; 128/760

[56] References Cited

U.S. PATENT DOCUMENTS

| 4,506,691 | 3/1985 | Tseo . |
| 4,819,684 | 4/1989 | Zaugg et al. . |
| 5,098,405 | 3/1992 | Peterson et al. . |

FOREIGN PATENT DOCUMENTS

240590A1  10/1987  European Pat. Off. .
370997A2  5/1990  European Pat. Off. .

*Primary Examiner*—Mark Bockelman
*Attorney, Agent, or Firm*—Knobbe, Martens, Olson, & Bear, LLP

[57] ABSTRACT

A medical connector is for use in transferring fluids to and from a patient. The connector has a primary conduit, which has an upstream branch in fluid communication with a primary source of fluid and a downstream branch in fluid communication with a patient. The connector also has a secondary conduit in fluid communication with said primary conduit. Additionally, the connector has a hollow, resilient valve positioned such that the primary fluid can flow through the valve when the valve is in a decompressed state. The valve has a tab extending into the secondary conduit such that a luer inserted in the secondary conduit compresses the tab, thereby preventing flow of the primary fluid through the connector while permitting both flow of fluid to the patient from the luer and flow of fluid from the patient to the luer.

6 Claims, 23 Drawing Sheets

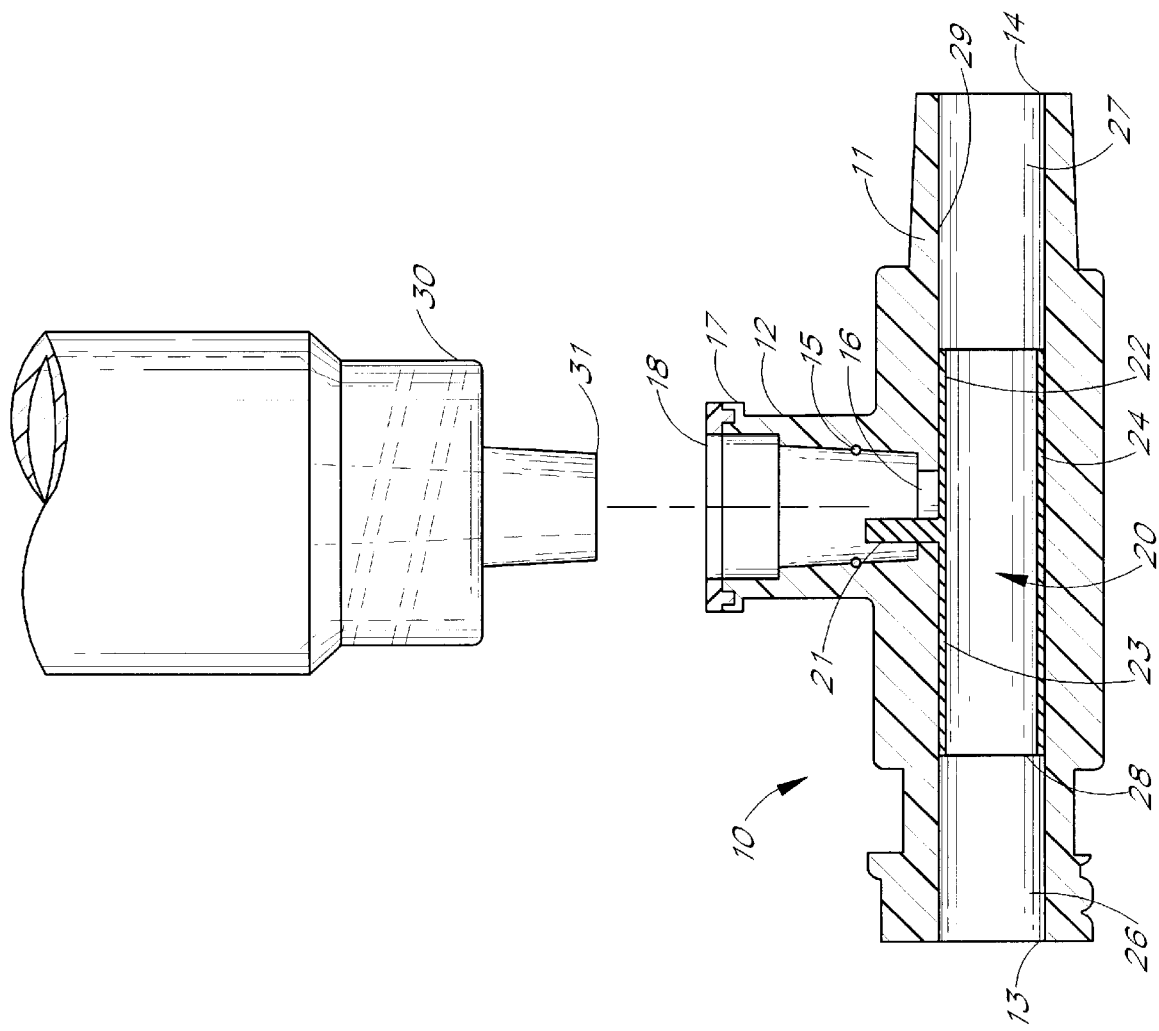

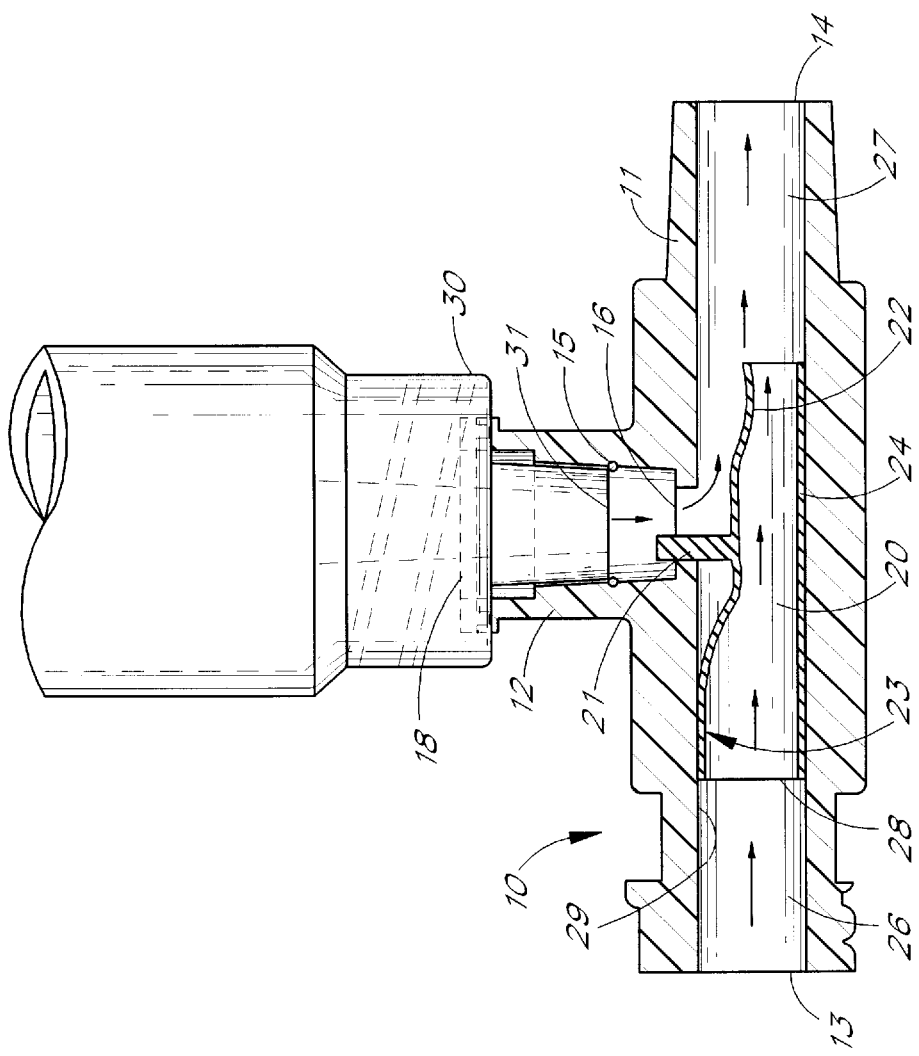

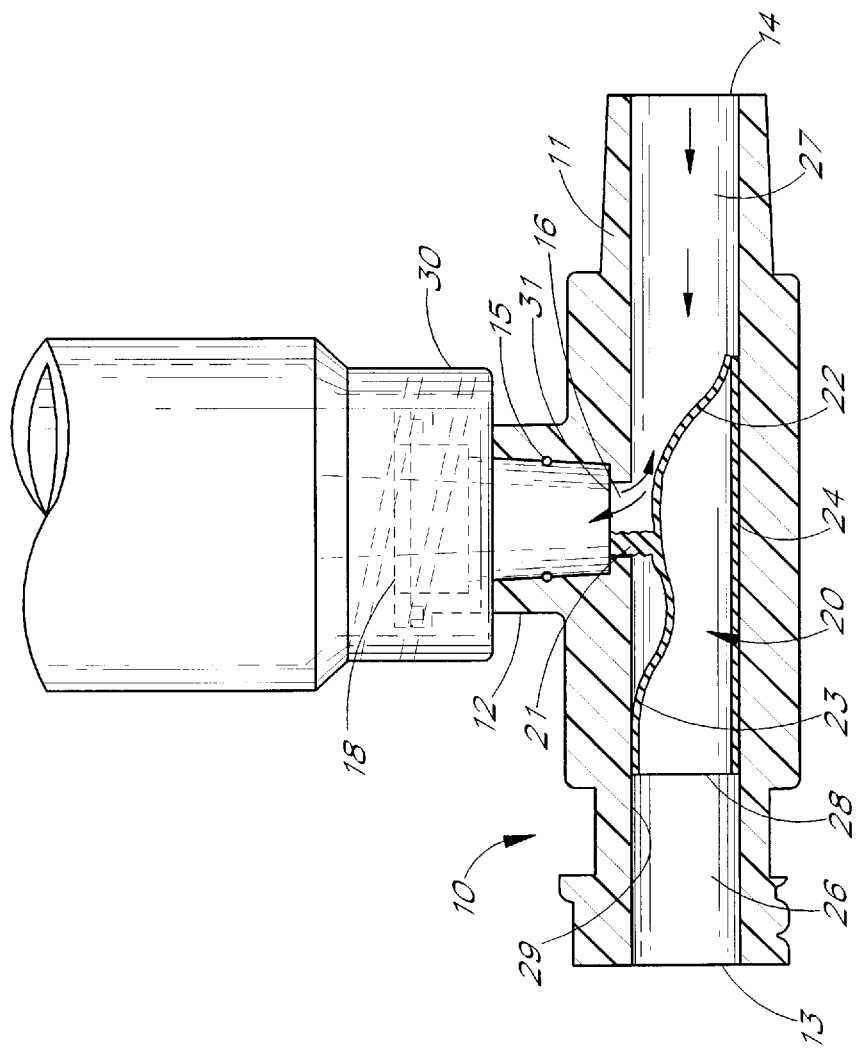

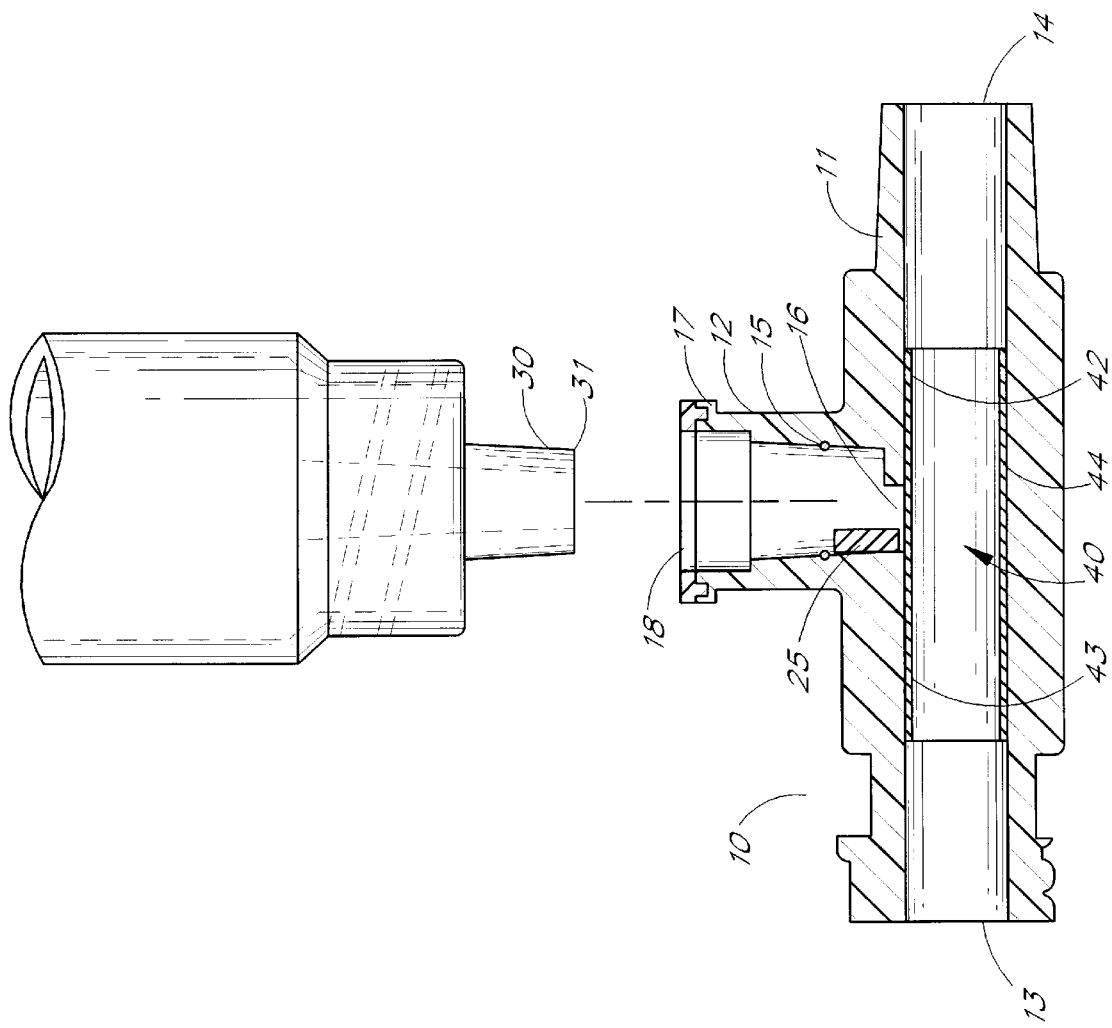

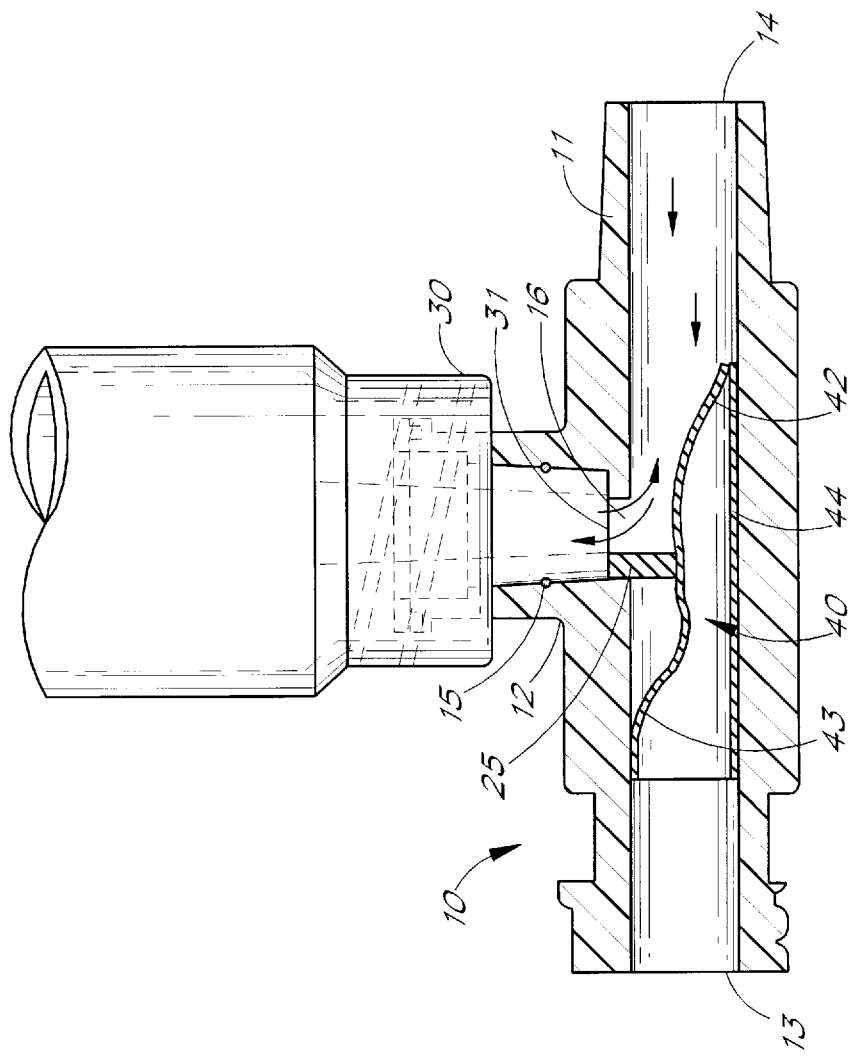

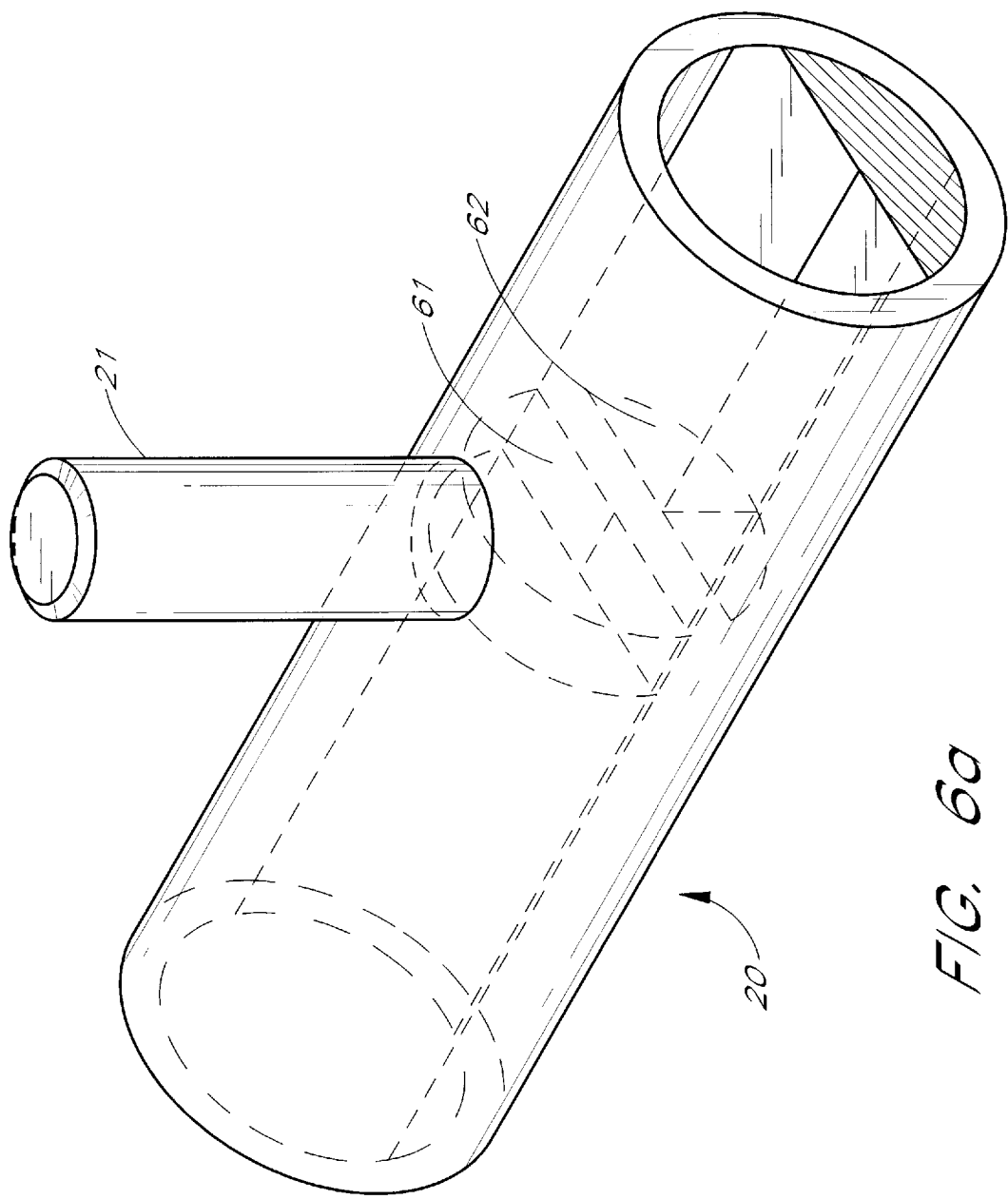

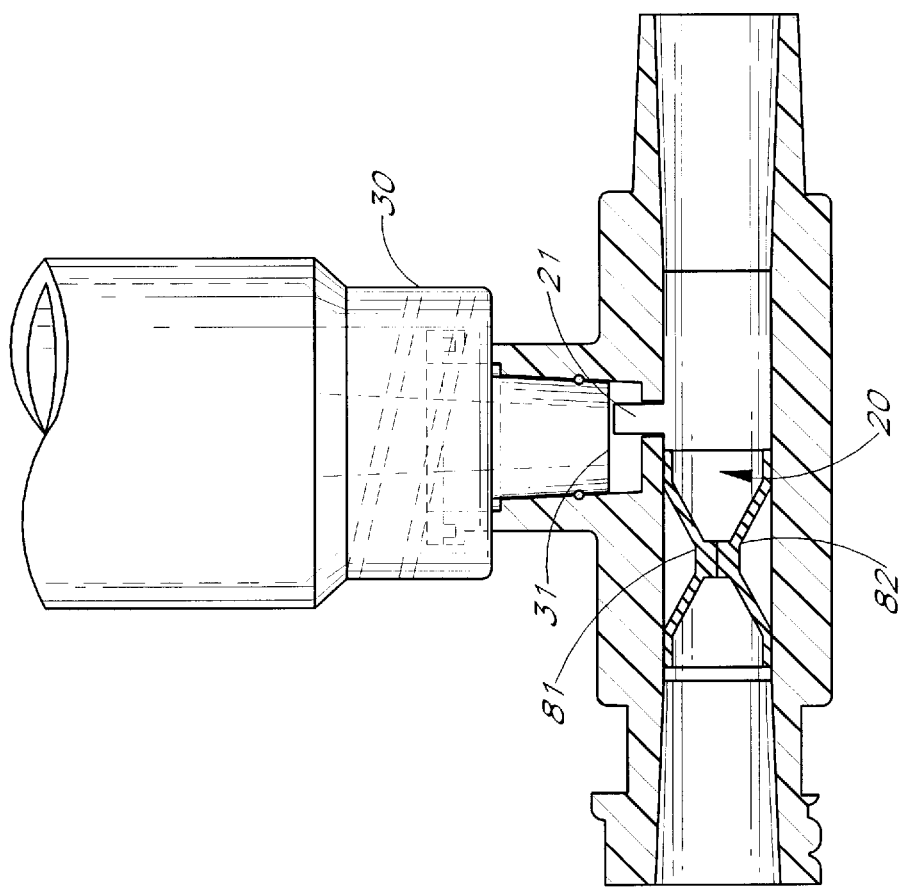

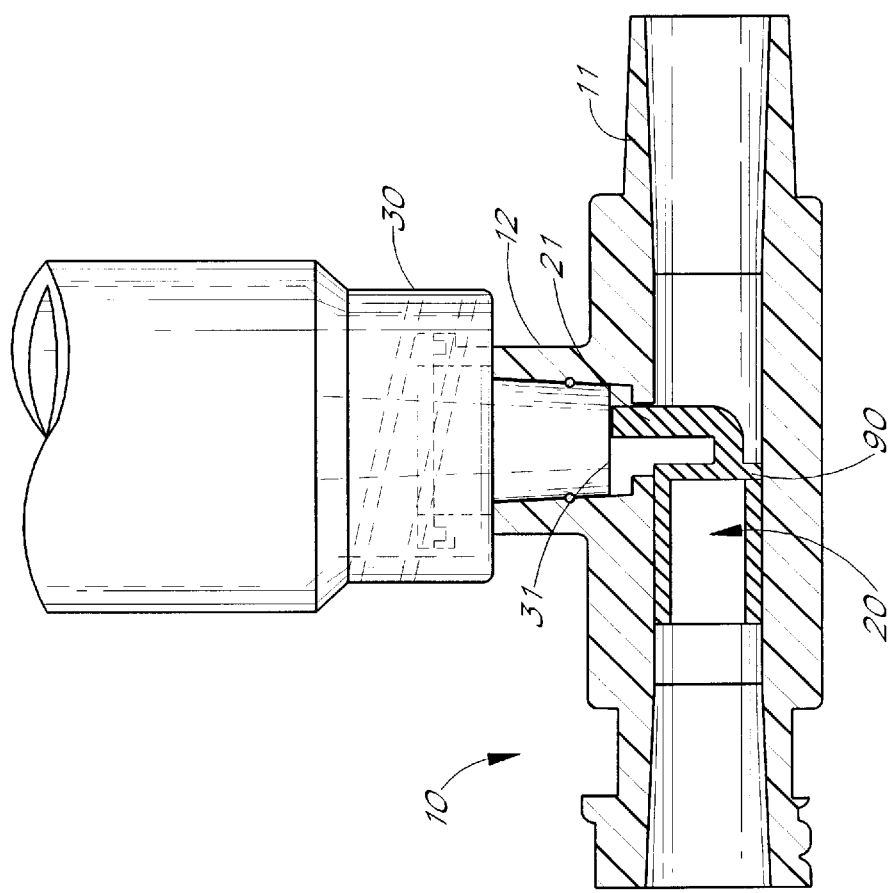

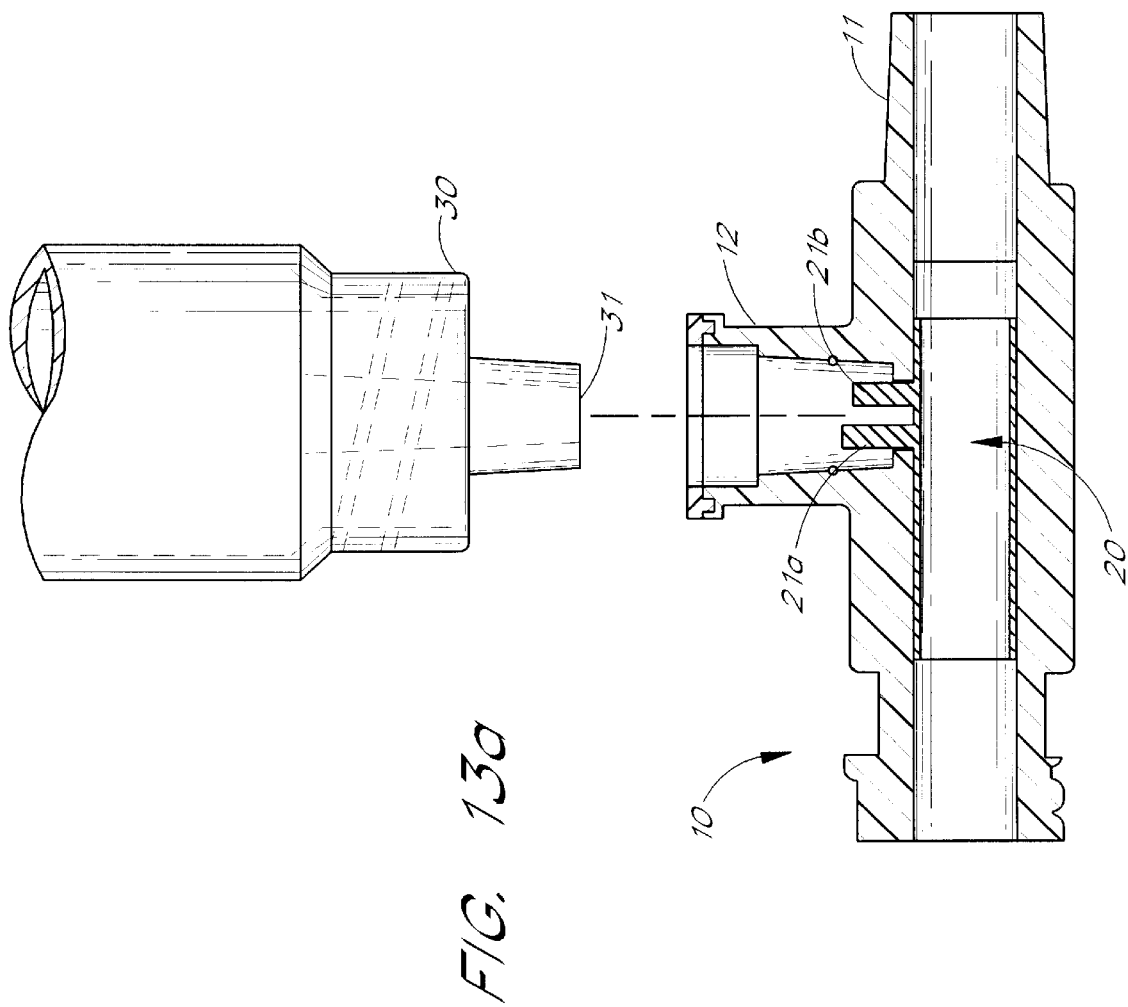

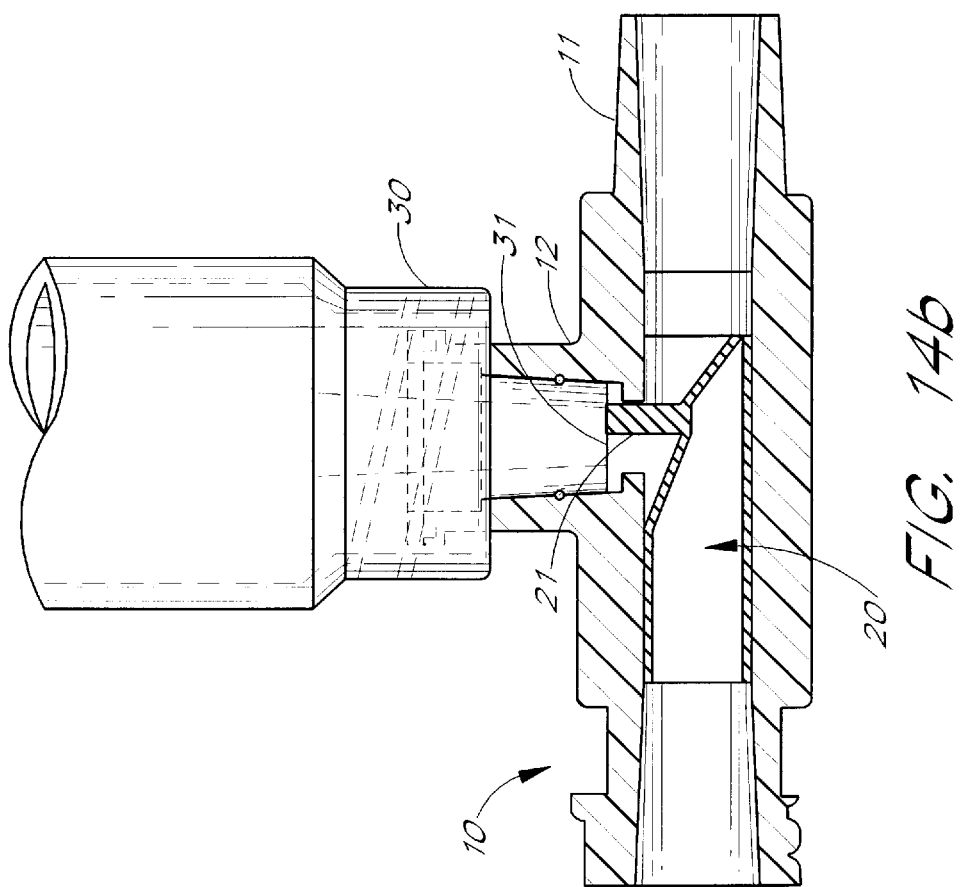

MEDICAL CONNECTOR

BACKGROUND OF THE INVENTION

1. Field of the Invention

This invention relates to the field of medical devices using a valve for transferring medication intravenously from one location to another. More specifically, this invention is directed to an improvement in medical valves to ensure that the patient receives the entire dosage of medication, while also providing a means for withdrawing blood from the patient.

2. Background Discussion

The manipulation of fluids for parenteral administration in hospital and medical settings routinely involves the use of connectors for facilitating the movement of fluids between two points. Oftentimes it is desirable to have the patient receive medication from a number of different sources using the same IV. Such a system may be accomplished, for example, by using a Y-connector, a piggy-back connector, a T-connector, or a manifold. Such devices have at least one secondary conduit connected with the primary conduit to add one or more secondary fluids, such as drugs, for example, to the primary fluid being infused into a patient through the primary conduit.

Many connectors or valves, especially those employing several mechanical components, have a relatively high volume of fluid space within them. A serious problem in the medical field has been the existence of this "dead space" at the intersection between the arm and the main bore in medical connectors which prevents the patient from receiving the full dosage of medication, since some of the medicine remains in the dead space of the connector. For example, in several prior art manifolds the operator inserts a syringe into the secondary conduit to introduce a secondary fluid into the primary fluid stream. However, because of the dead space that exists between the end of the syringe and the primary conduit passage, some of the secondary fluid will remain in the junction between the secondary conduit and the primary conduit.

Previous valving devices have focused on removing the undesirable dead space in such devices.

A one-way valving apparatus formed in a manner such that creation of undesirable volumetric dead space is substantially precluded is shown in U.S. Pat. No. 4,666,429 to Stone and U.S. Pat. No. 3,416,567 to Von Dardel et al. In the several embodiments described, a movable element is positioned adjacent to the inner wall of the primary conduit at the junction between the secondary and primary conduits so that the movable element forms a one-way valve. The design of the secondary conduit allows the tip of a syringe nozzle to be substantially adjacent to the movable element. The movable element is partially displaced due to fluid pressure from the flow of secondary fluid through the secondary conduit toward the primary conduit thereby allowing the secondary fluid to pass by the movable element and enter the primary conduit stream. Once the secondary fluid passes through the junction, the movable element returns to its original position, blocking the junction between the primary and secondary conduits.

In the intravenous environment, it is often desirable to utilize a device having the capability of both introducing fluid medication or withdrawing blood from a patient. However, the movable element of the '429 and '567 patents provide only one-way fluid flow, since the movable element is not displaced due to fluid flow in the primary passageway, and therefore, fluid from the patient cannot be drawn into the secondary conduit. Two-way valves are advantageous for drawing a patient's blood back to determine if the IV system is properly inserted into a patient's vein to provide medication. Further, two-way valves have the additional advantage of having the capacity to withdraw blood samples from the patient.

An example of a two-way valve is shown in U.S. Pat. No. 5,269,771 to Thomas, et al. A hollow plunger means is extended through the valve means within a housing to provide free fluid communication between the inlet and the outlet of the device through the central passageway of the plunger means. A syringe coupled to the inlet may then introduce fluid to the patient or, in the alternative, withdraw fluid from the patient.

A serious drawback to this prior art device is the large amount of volumetric dead space that exists not only within the central passageway of the plunger means, but also within the passageways of the housing. Thus, a large amount of the medication to be transferred to the patient remains in the dead space, thereby preventing the delivery of an exact amount of medication. The delivery of an exact amount of medication may be critical in some situations when chemotherapeutic agents are being administered or small children are being treated. An inexpensive medical connector for transferring medication from a number of different sources using the same IV wherein dead space is minimized and fluid in the secondary conduit is bidirectional would be of great benefit to the medical community.

SUMMARY OF THE INVENTION

The medical connector of this invention has several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of the Drawings," one will understand how the features of this invention provide advantages which include safety, reliable and repeatable performance, simplicity of manufacture and use, eradication of dead space, and capacity for one-way or two-way fluid flow.

The present invention relates to a valve positioned at the intersection of a primary conduit and a secondary conduit of a medical connector. The valve of the present invention is a hollow, resilient tube oriented along the longitudinal axis of the primary conduit. The tube, in its resting state, blocks the fluid path to and from the secondary conduit. The primary conduit has an inlet at its upstream end and an outlet at its downstream end. The primary conduit has an upstream portion defined by the portion between the upstream end and the junction with the secondary conduit, as well as a downstream portion defined by the portion between the downstream end and the junction. Fluid passing through the primary conduit will pass through the hollow valve, but will not be able to enter the secondary conduit of the connector. Extending from the exterior side wall of the valve and into the secondary conduit cavity is a tab that is positioned off-center within the cavity of the second conduit. The outer diameter of the valve is slightly larger than the inner diameter of the primary conduit of the connector to ensure a fluid-tight fit.

The secondary conduit may be frusto-conically shaped so as to receive a standard tapered male luer. A luer inserted into the secondary conduit may be located in one of two positions. At a first position the tip of the male luer contacts and rests on an annular ring or other protrusion that is integral with or attached to the inner wall of the secondary conduit a short distance above the tab of the valve. The annular ring or protrusion may be manufactured of the same plastic or other medically inert material that the medical connector is manufactured from. Alternatively, a tab may be provided within the secondary conduit to provide the same function as the annular ring.

To inject fluid from the secondary conduit to the patient, the luer is inserted to the first position and fluid from a syringe or other medical device in fluid communication with the luer is introduced into the secondary conduit, whereby the resulting fluid pressure partially displaces the resilient valve, allowing fluid from the syringe to pass through the luer and beyond the tube into the primary conduit. Once the fluid from the syringe has passed into the primary conduit, the resilient valve returns to its original shape, stopping fluid communication between the primary and secondary conduits. Because the distance between the tip of the luer at the first position with respect to the valve is so small, any dead space at the junction between the secondary conduit and the primary conduit is minimized. At the first position, the medical connector and valve of the present invention perform as a fluid pressure-activated one-way valve. Moreover, while the luer is at the first position, primary fluid continues to flow through the primary conduit from the upstream end thereof to the downstream end thereof.

To withdraw fluid from the patient into the secondary conduit, the tip of the luer is pushed further downward and rides over the annular ring or other protrusion, making an auditory "clicking" sound. The clicking sound informs the operator that the luer is located in the second position within the secondary conduit. In the second position the edge of the luer tip engages the tab of the valve and forces the tab downward. As the tab is pushed downward into the primary conduit, the walls of the valve accordingly are biased downward and the valve collapses to close off primary fluid flow through the primary conduit upstream of the intersection of the primary and secondary conduits.

With the male luer in the second position, the valve is maintained in its collapsed position, providing an open passageway to withdraw fluid from the patient to the secondary conduit while effectively maintaining a seal barring fluid flow through the upstream portion of the primary conduit. Since primary fluid flow is sealed off by the collapsed valve, no clamp is required in the primary conduit to pinch off the conduit and prevent primary fluid flow during withdrawal of fluid from the patient. Furthermore, the portion of the valve upstream of the junction maintains a fluid-tight seal against the inner walls of the primary conduit. Such a configuration ensures that no primary fluid is mixed with the patient's blood as the blood is withdrawn into the secondary conduit. Thus, the present invention provides a pressure-activated valve for injecting fluid into the patient, as well as a luer-activated valve for withdrawing fluid from the patient.

Due to the novel features of the present invention, the present invention overcomes a key problem in the prior art since it provides a one-way and two-way valve with minimal dead space while also being inexpensive to manufacture.

In an alternate embodiment, instead of employing a tab attached to the valve to compress the valve, a movable tab may be attached to the inner wall of the secondary conduit. In this embodiment the tip of the male luer contacts and biases the movable tab downward. In turn, the movable tab forces the resilient valve down to a position where the valve collapses and seals off the primary conduit from primary fluid flow while providing open fluid flow communication between the secondary conduit and the patient.

BRIEF DESCRIPTION OF THE DRAWINGS

The preferred embodiments of this invention, illustrating its features, will now be discussed in detail. These embodiments depict the novel and nonobvious medical connector of this invention shown in the accompanying drawings, which are for illustrative purposes only. These drawings include the following figures, with like numerals indicating like parts:

FIG. 1 is a partial cross-sectional view of the valve of the present invention in a closed position within a medical connector.

FIG. 2 is a partial cross-sectional view of the valve of the present invention in the open position within a medical connector for injecting fluid into a patient.

FIG. 3 is a partial cross-sectional view of the valve of the present invention in an open position within a medical connector for withdrawing fluid from the patient.

FIG. 4 is a partial cross-sectional view of an alternate embodiment of the medical connector of the present invention wherein the valve is in a closed position.

FIG. 5 is a partial cross-sectional view of the alternate embodiment of the present invention shown in FIG. 4 wherein the valve is in an open position for withdrawing fluid from the patient.

FIG. 6a is a perspective view of an alternate embodiment of valve of the present invention showing the valve in a closed position.

FIG. 6b is a partial cross-sectional perspective view of valve shown in FIG. 6a.

FIGS. 10a and 10b are cross-sectional views of an alternate embodiment of the present invention showing the valve in a closed position and an open position, respectively.

FIGS. 12a and 12b are cross-sectional views of an alternate embodiment of the present invention showing the valve in a closed position and an open position, respectively.

FIGS. 13a and 13b are cross-sectional views of an alternate embodiment of the present invention showing the valve in a closed position and an open position, respectively.

FIGS. 14a and 14b are cross-sectional views of an alternate embodiment of the present invention showing the valve in a closed position and an open position, respectively.

DETAILED DESCRIPTION OF THE DRAWINGS

Figure 6B:
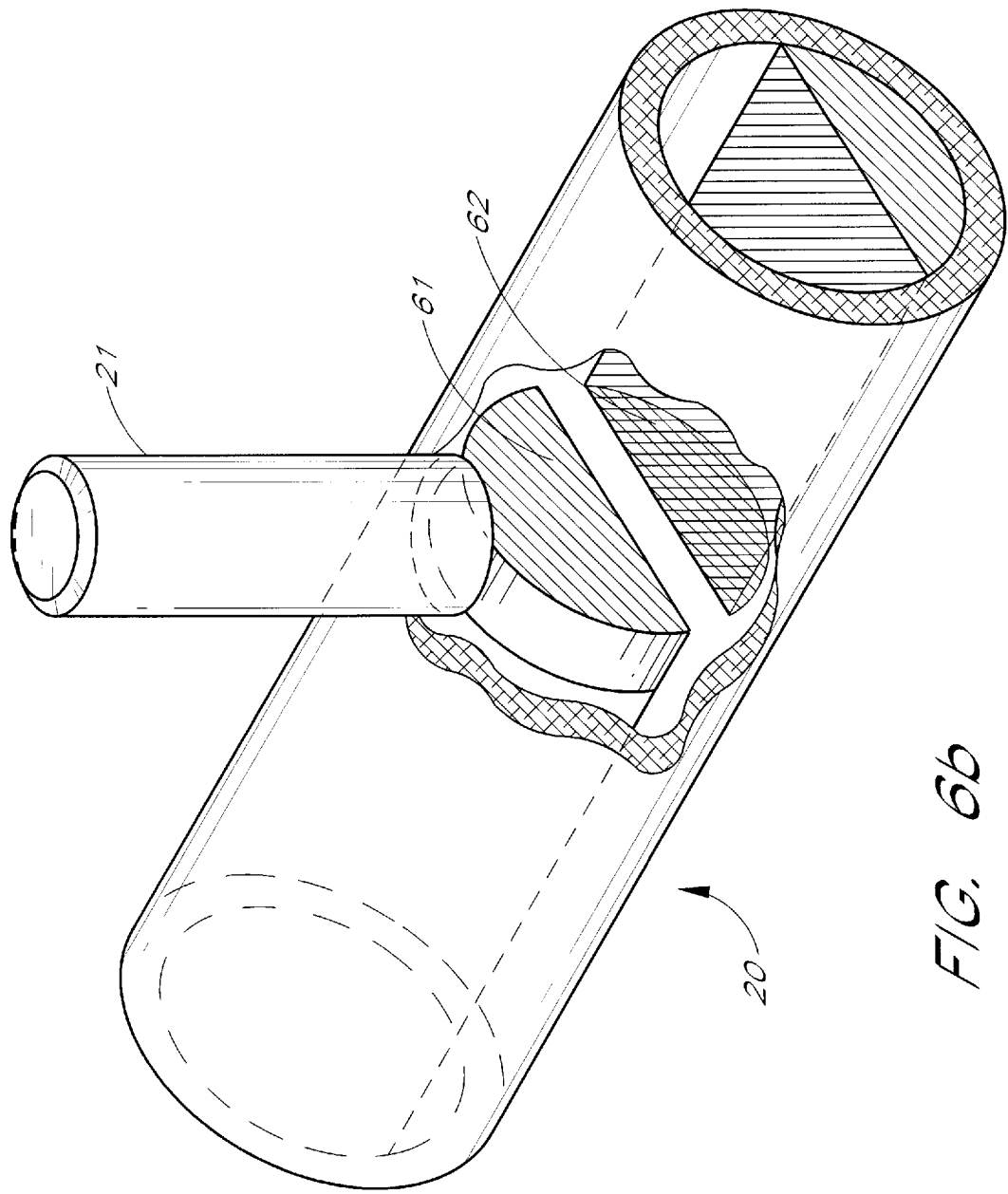

FIG. 1 illustrates a preferred embodiment of the medical connector 10 of the present invention where the valve 20 is in the closed position. Medical connector 10 comprises a primary conduit 11 in fluid communication with a secondary conduit 12 at junction 16. The primary conduit 11 has an inlet 13 at its upstream end and an outlet 14 at its downstream end. The primary conduit 11 has an upstream portion 26 defined by the portion between the upstream end (inlet 13) and the junction 16 with the secondary conduit 12, as well as a downstream portion 27 defined by the portion between the downstream end (outlet 14) and the junction 16. Valve 20 is preferably located at junction 16. The longitudinal axis of valve 20 is in alignment with the longitudinal axis of primary conduit 11. Positioned at junction 16 of medical connector 10, valve 20 in its uncompressed state prevents any fluid flow between secondary conduit 12 and primary conduit 11. Valve 20 comprises a hollow, resilient tube 24 and tab 21, where the tube 24 is further defined by upstream wall section 23 and downstream wall section 22. Tab 21 of valve 20 extends from the side wall of valve 20 into secondary conduit 12. Valve downstream wall section 22 extends a short distance downstream in primary conduit 11 beyond junction 16, and valve upstream wall section 23 may extend comparatively a longer distance upstream past junction 16. Along the inner walls of secondary conduit 12 is annular ring 15 positioned slightly above tab 21 of valve 20. Preferably, the cavity of secondary conduit 12 tapers inwardly so that secondary conduit 12 may be adapted to fit snug with an ANSI (American National Standards Institute, Washington, D.C.) standard end of a medical implement. Typically, the implement is a syringe, luer, or any one of a wide variety of conduits used in medical applications. A luer is defined as any tube for fluid communication and may also be commonly used with a medical implement. Luers may vary in shape and can be conical, cylindrical, or any other shape known to those of skill in the art. The secondary conduit 12 is defined by a proximal end 18 and a distal end which is at junction 16. Advantageously, the proximal end 18 of secondary conduit 12 can be equipped with a locking mechanism to facilitate locking of secondary conduit 12 to a variety of medical implements or connector devices. For example, referring to FIG. 1, locking ears 17 near the proximal opening 18 of secondary conduit 12 are preferably provided, such that the secondary conduit 12 can be locked into any compatible luer-lock device known to those of skill in the art.

As configured, during operation fluid from a primary fluid source (not shown) enters inlet 13 of primary conduit 11 and flows through tube 24 of valve and out outlet 14 of primary conduit 11 for transmission to the patient. The outer diameter of tube 24 is preferably slightly larger than the inner diameter of primary conduit 11. Therefore, a fluid-tight fit is ensured between the valve 20 and the inner wall 29 of the primary conduit 11 to prevent any primary fluid flowing in between the walls of tube 24 and primary conduit 11 and into secondary conduit 12. With the valve 20 in this configuration, no fluid is allowed to flow between secondary conduit 12 and primary conduit 11.

Upon injection of fluid from a medical implement 30 into secondary conduit 12, one-way valving is provided for fluid flow from the medical implement 30 into primary conduit 11 and to the patient. To inject fluid from the secondary conduit 12 to the patient, the medical implement 30 is inserted into a first position in secondary conduit 12 and fluid from a medical implement 30 is introduced into secondary conduit 12.

As shown in FIG. 2, the proximal end 31 of medical implement 30 is inserted into secondary conduit 12 until proximal end 31 contacts annular ring 15. Because annular ring 15 is positioned to be a very short distance from junction 16, dead space between proximal end 31 of medical implement 30 and junction 16 is minimized. With the edges of proximal end 31 resting on annular ring 15, medical implement 30 is in a first position whereupon by injecting fluid through medical implement 30, the resulting fluid pressure partially deflects resilient tube 24 to allow the secondary fluid from medical implement 30 to pass beyond valve 20 and into primary conduit 11 and into the patient. After the secondary fluid from medical implement 30 has passed through junction 16, resilient tube 24 decompresses and returns to its original shape. The ability of tube 24 of valve 20 to compress under fluid pressure and to return to its original shape is determined by the resiliency of the material used to manufacture the valve 20. By immediately returning to its original shape upon termination of fluid pressure from the medical implement 30, valve 20 prevents any back flow of fluid from outlet 14 to secondary conduit 12. Moreover, because upstream wall section 23 is longer than downstream wall section 22, the fluid pressure introduced by medical implement 30 is not great enough to push the upstream end 28 of tube 24 to overcome its fluid-tight seal with the walls of primary conduit 11. Thus, during this procedure, primary fluid flow from inlet 13 into secondary conduit 12 is prevented. Alternatively, the valve 20 may be manufactured from a material that does not require the upstream portion 23 of the tube 24 to be longer than the downstream portion 22 of the tube 24 while still achieving the advantages of the present invention.

FIG. 3 illustrates the two-way valving feature of the present invention. As shown in FIG. 3, proximal end 31 of medical implement 30 biases tab 21 downward, thereby compressing and maintaining tube 24 in an open, fluid communication position. In order to withdraw a sample of fluid from the patient, proximal end 31 of medical implement 30 is pushed over annular ring 15, thereby providing an auditory "click" sound as the medical implement 30 is set in the second position. This "click" sound is an audible signal which a user may rely upon to indicate that medical implement 30 is locked into the second position within secondary conduit 12. Alternatively, the user may be able to determine the position of the medical implement 30 in the secondary conduit 12 by touch and sight, and a audible click would be unnecessary.

The edge of proximal end 31 of medical implement 30 biases tab 21 downward into the passageway of primary conduit 11. Tab 21 of valve 20 is specifically designed to be positioned off-center within junction 16 to allow the edge of proximal end 31 to contact tab 21 when medical implement 30 is in the second position. Tab 21 can be positioned off-center towards any side of secondary conduit 12. However, in certain embodiments, it is desirable to position tab 21 closer to the downstream end of primary conduit 11.

In response to the displacement of tab 21, tube 24 collapses, as shown in FIG. 3, to close off any primary fluid flow in primary conduit 11 from inlet 13. Additionally, upstream wall section 23 also is displaced into the passageway of primary conduit 11, but because upstream wall section 23 is comparatively longer than downstream wall section 22 or alternatively, the strength of the material of the tube 24 does not cause separation of the upstream wall section 23 from the inner walls 29 of primary conduit 11 upstream of the junction 16, the force from medical implement 30 is not great enough to displace the upstream end 28 of upstream wall section 23 from its fluid-tight fit against the inner walls 29 of primary conduit 11. Thus, primary fluid flowing into inlet 13 is completely blocked from entering secondary conduit 12. With an open passageway maintained between outlet 14 and secondary conduit 12 through primary conduit 11, an operator may draw a fluid sample from the patient into medical implement 30. Alternatively, the two-way valving feature allows an operator to draw back a small amount of fluid from the patient into medical implement 30 to determine whether the IV system is inserted into the patient's vein so that medication may be safely and properly transmitted to the patient.

Advantageously, a clamp is not required to pinch off primary fluid flow in primary conduit 11 when withdrawing fluid from the patient, since valve 20 collapses down to effectively seal off conduit 11 when medical implement 30 is in the secondary position in secondary conduit 12. Thus, when luer 30 is placed in the first position, valve 20 acts as a pressure-activated one-way valve for injecting fluid into a patient; and when luer 30 is placed in the second position, valve 20 acts as a two-way valve for introducing or withdrawing fluid from the patient. Due to the limited number of components, the medical connector of the present invention is inexpensive and easy to manufacture.

An alternate embodiment of the two-way valving apparatus with minimal dead space is illustrated in FIG. 4. In the alternate embodiment, valve 20 is a hollow, resilient tube residing within primary conduit 11 at junction 16. As in the preferred embodiment illustrated in FIGS. 1–3, valve 20 comprises a tube 24 having a upstream wall section 23 and a downstream wall section 22. Instead of having a tab connected to tube 44, a tab 25 is attached to the inner wall of conduit 12 adjacent junction 16 and beneath annular ring 15. Tab 25 serves primarily the same function as tab 21 of FIGS. 1–3 to maintain downstream wall section 42 of valve 40 in a deformed position so as to provide fluid communication between secondary conduit 12 and primary conduit outlet 14 when medical implement 30 is in the second position. FIG. 5 illustrates medical implement 30 in the second position within secondary conduit 12. Upon riding proximal end 31 of medical implement 30 over annular ring 15 and into the second position, the edge of proximal end 31 biases tab 25 downward into the passageway of primary conduit 11 to displace valve 40 from blocking junction 16, and collapsing downstream wall section 42 to close off upstream primary fluid flow from primary conduit inlet 13. Upon withdrawal of medical implement 30 from the second position within secondary conduit 12, tab 25 returns to its natural position within secondary conduit 12, allowing resilient tube 44 of valve 40 to return to its original shape.

Alternatively, annular ring 15 may be substituted for a tab, a protrusion, a ramp, or any other structure known to those of skill in the art. Preferably, annular ring 15 is made of the same material as medical connector 10, that being a plastic or any other medically inert material.

Figure 7A:
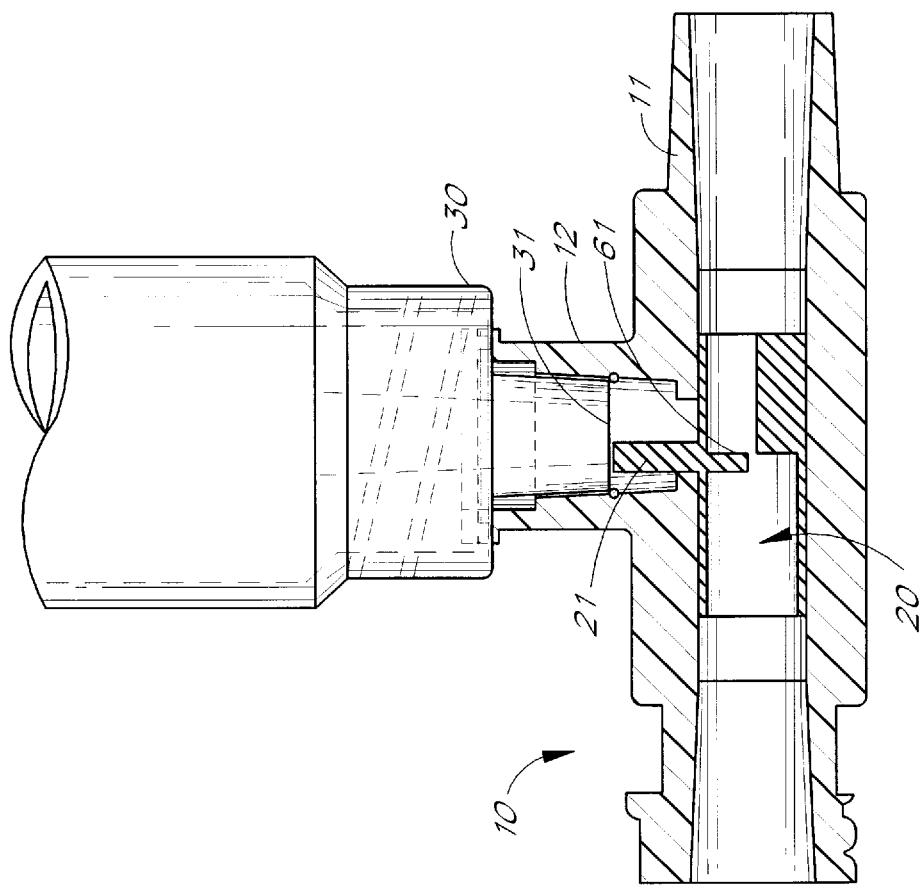
FIGS. 7a and 7b are cross-sectional views of the alternate embodiment of the valve of the present invention shown in FIGS. 6a and 6b where the valve is shown in a closed position and an open position, respectively.
Figure 7B:
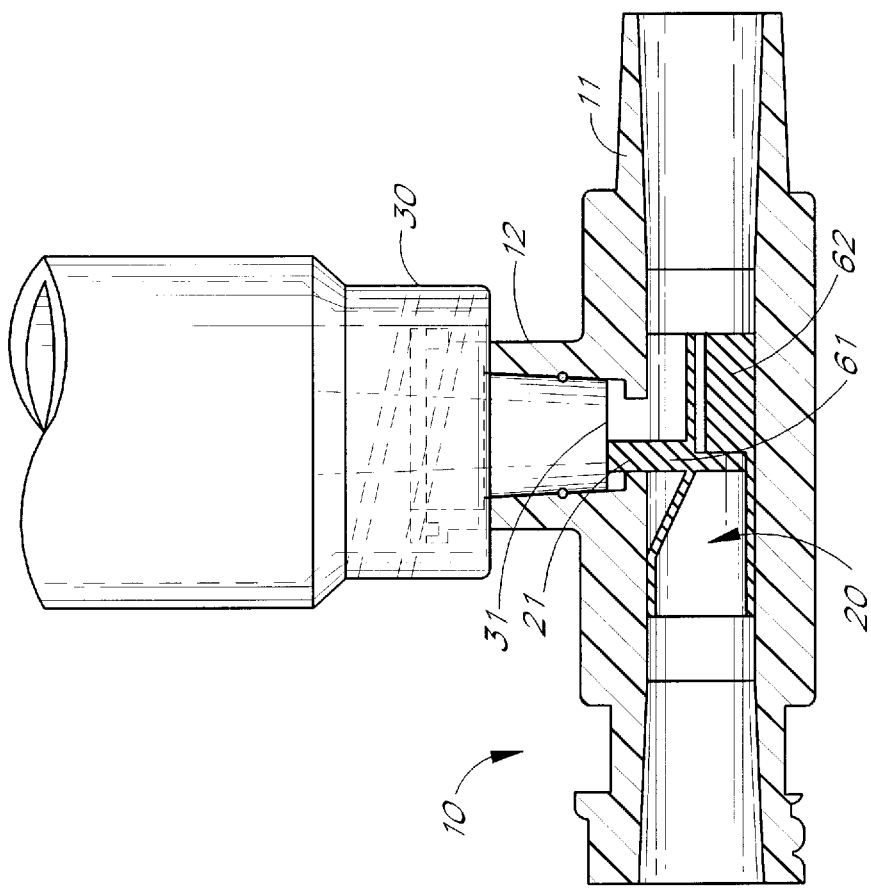

FIGS. 6a and 6b show an alternate embodiment of valve 20 of the present invention that may be used in medical connector 10. Valve 20 in FIGS. 6a and 6b have tab 21 and tube 24 with inner blocks 61 and 62 which seal off upstream primary fluid flow when tab 21 is pressed down by medical implement 30 in the second position. FIGS. 7a and 7b further illustrate the functioning of the alternate embodiment of the valve 20 shown in FIGS. 6a and 6b. FIG. 7a shows the valve 20 in the closed position, while FIG. 7b shows the valve 20 in the open position.

Figure 8A:
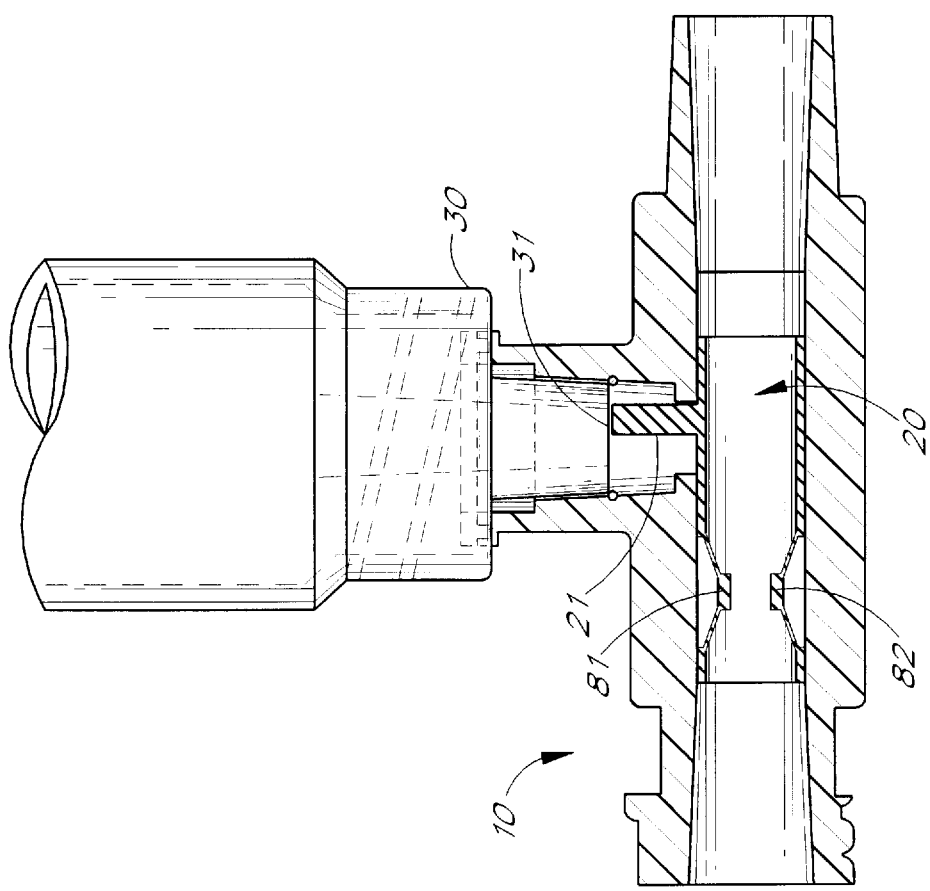
FIGS. 8a and 8b are cross-sectional views of an alternate embodiment of the present invention showing the valve in a closed position and an open position, respectively.
Figure 8B:
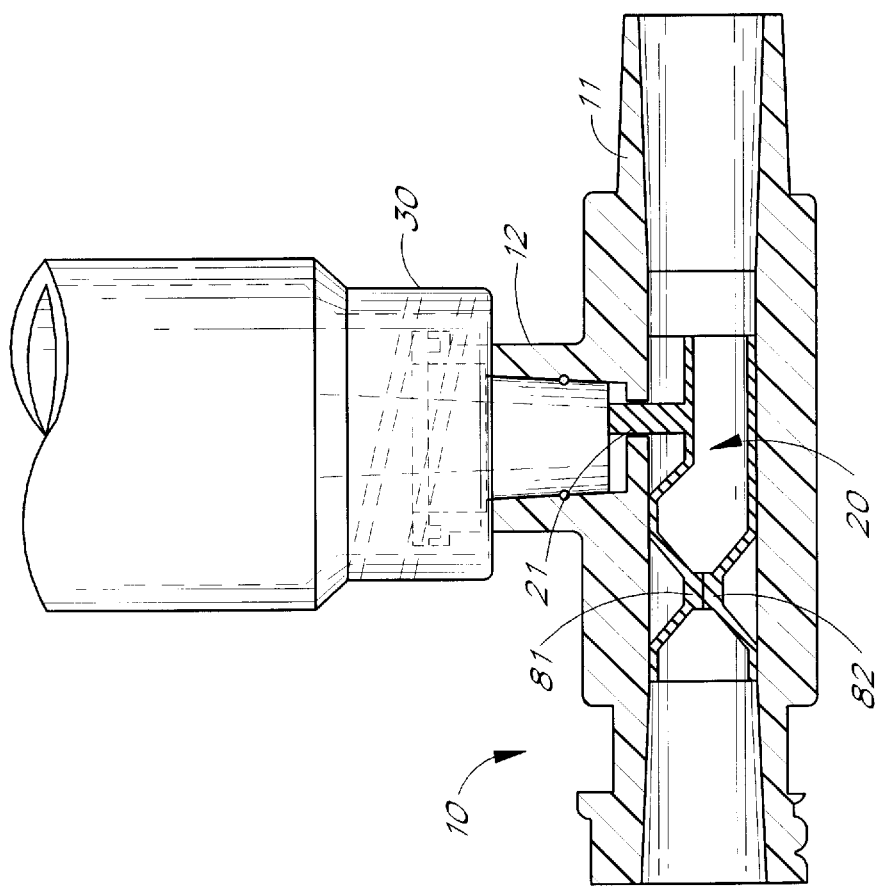

FIGS. 8a and 8b show another alternate embodiment of valve 20 of the present invention that may be used in medical connector 10. Valve 20 in FIGS. 8a and 8b have tab 21 and tube 24 with inner blocks 81 and 82 which seal off upstream primary fluid flow when tab 21 is pressed down by medical implement when medical implement 30 is in the second position. (FIG. 8b).

Figure 9A:
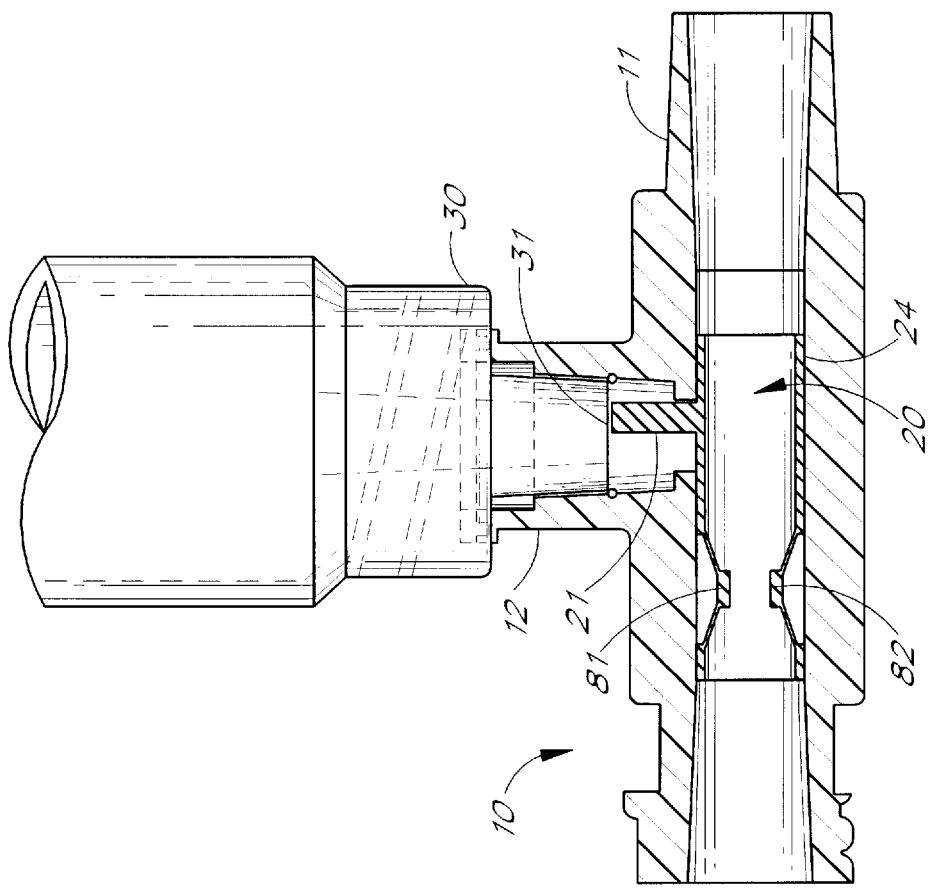
FIGS. 9a and 9b are cross-sectional views of an alternate embodiment of the present invention showing the valve in a closed position and an open position, respectively.
Figure 9B:
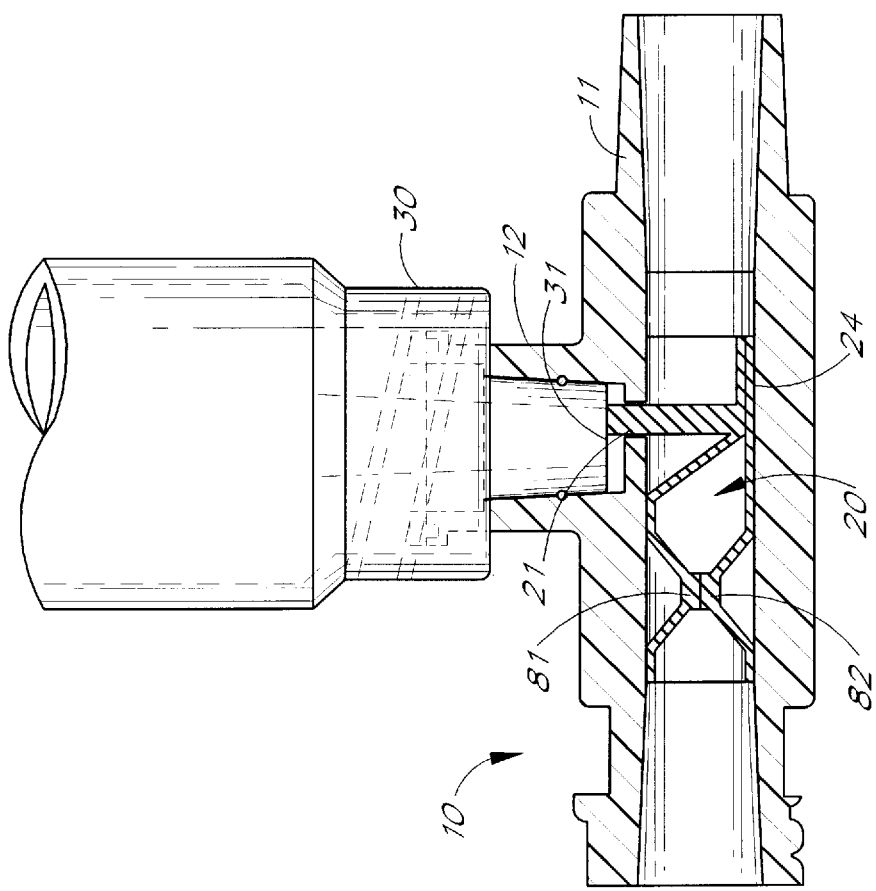

FIGS. 9a and 9b show another alternate embodiment of valve 20 of the present invention that may be used in medical connector 10. Valve 20 in FIGS. 9a and 9b have tab 21 and tube 24 with inner blocks 81 and 82 which seal off upstream primary fluid flow when tab 21 is pressed down by medical implement 30 when medical implement 30 is in the second position. Further, tube 24 also collapses when the tab 21 is compressed. (FIG. 9b).

Figure 10A:
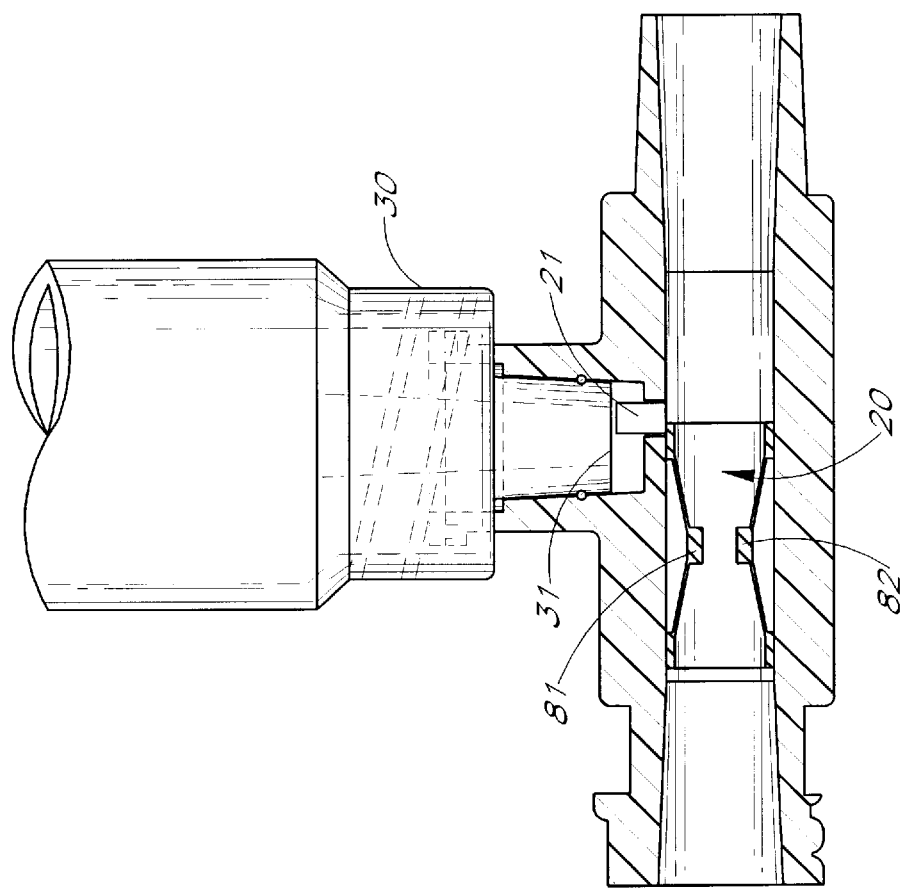

FIGS. 10a and 10b show another embodiment of the present invention. Two inner blocks 81 and 82 close off primary fluid flow when the medical implement 30 is in the second position with tab 21 compressed as shown in FIG. 10b.

Figure 11A:
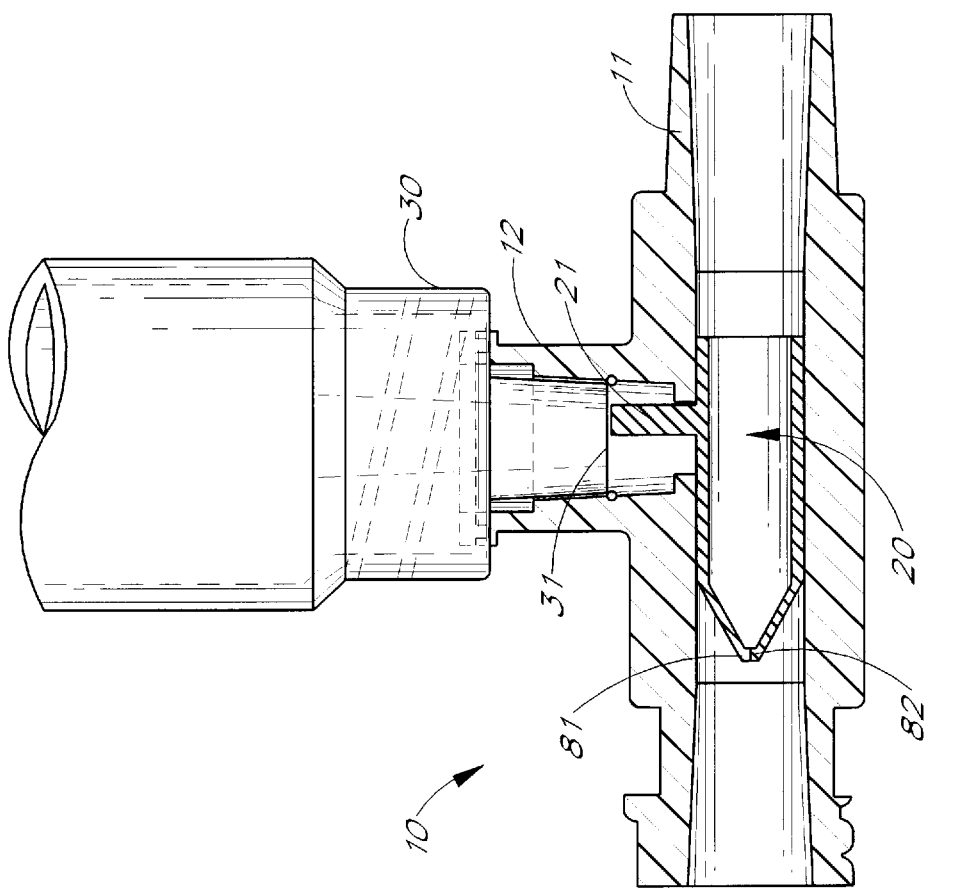
FIGS. 11a and 11b are cross-sectional views of an alternate embodiment of the present invention showing the valve in a closed position and an open position, respectively.
Figure 11B:
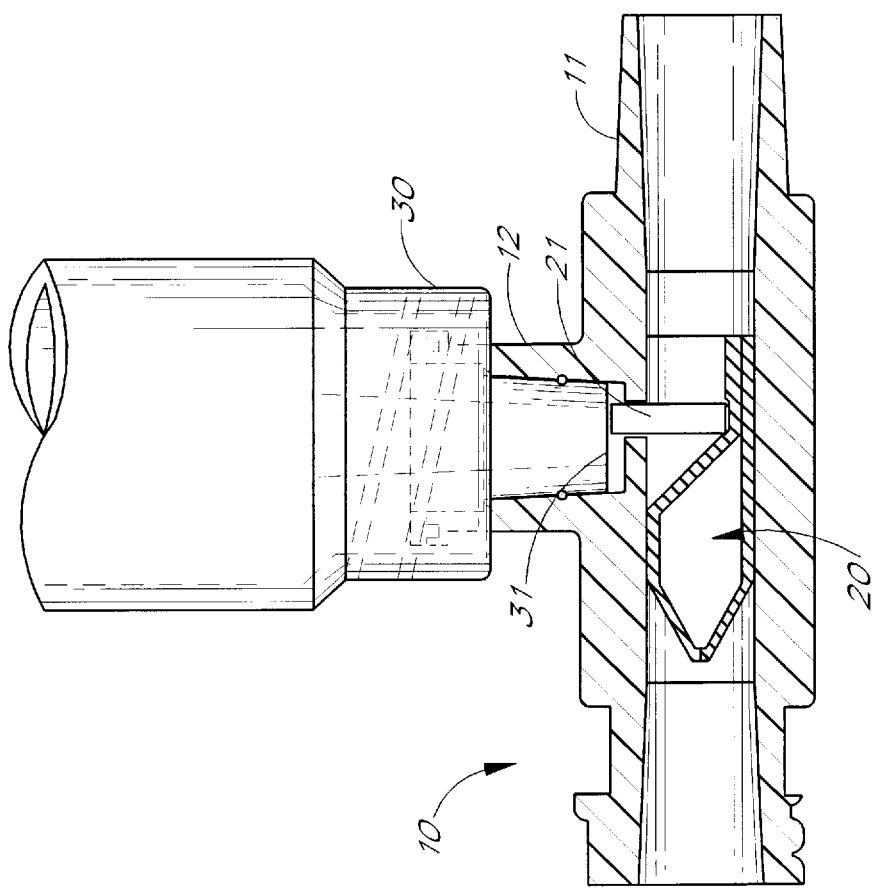

FIGS. 11a and 11b show another embodiment of the valve 20 of the present invention which seals off primary fluid flow upstream when tab 21 is compressed by medical implement 30 as shown in FIG. 11b.

Figure 12A:
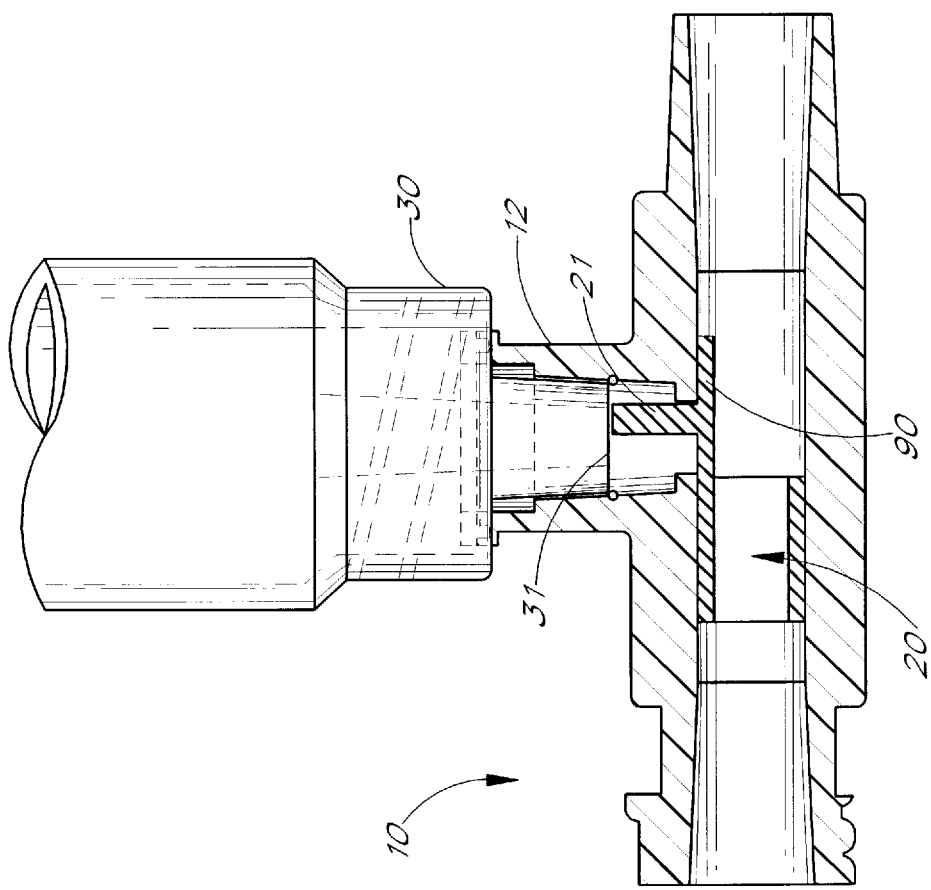

FIGS. 12a and 12b show another embodiment of the valve 20 of the present invention which seals off primary fluid flow upstream when medical implement 30 compresses the tab 21 as shown in FIG. 12b. Valve 20 comprises a tab 21 and a gate 90 where gate 90 seals off primary fluid flow upstream in primary conduit 11 when medical implement 30 is pushed into the second position, thereby biasing tab 21 downward and forcing gate 90 to close.

Figure 13B:
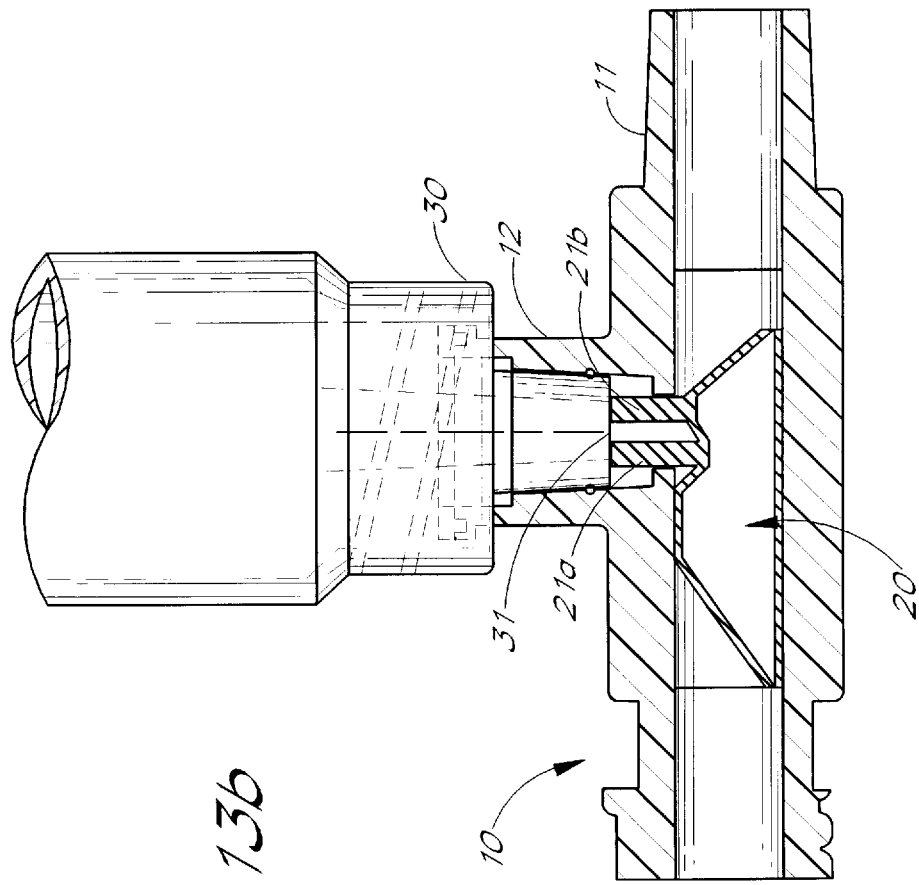

FIGS. 13a and 13b show another embodiment of the valve 20 of the present invention which seals off primary fluid flow upstream when medical implement 30 compresses the tab 21a or tab 21b as shown in FIG. 13b.

Figure 14A:
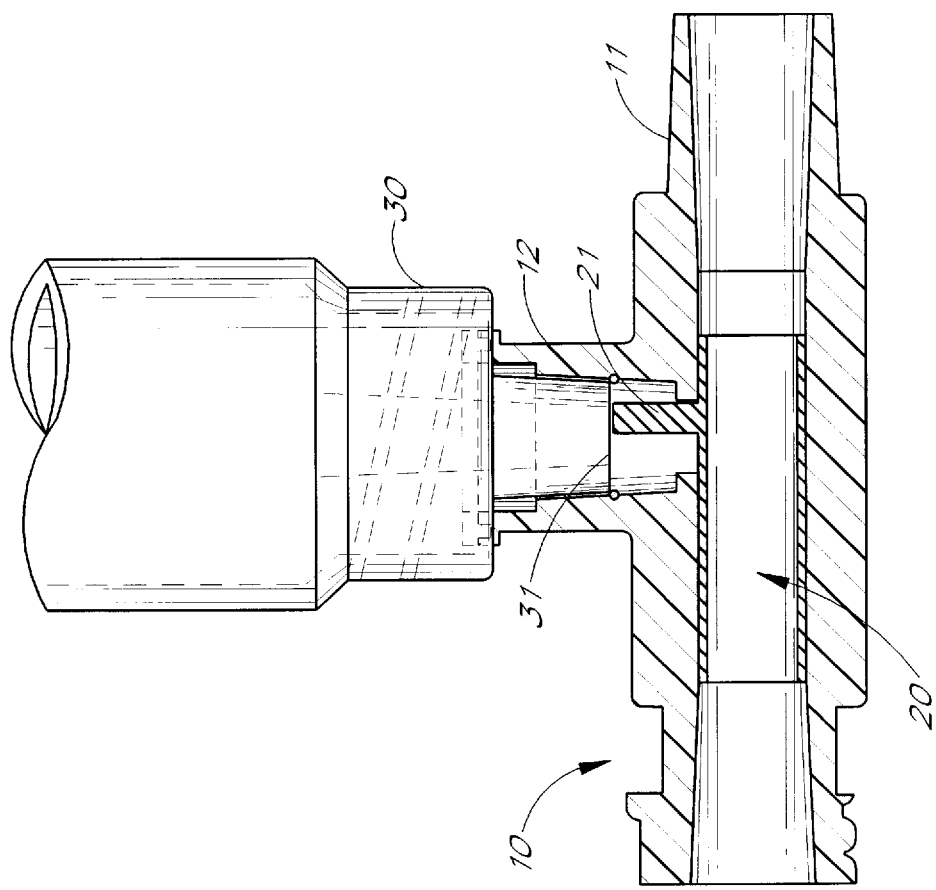

FIGS. 14a and 14b show another embodiment of the valve 20 of the present invention which seals off primary fluid flow upstream when medical implement 30 compresses tab 21 as shown in FIG. 14b.

SCOPE OF THE INVENTION

The above presents a description of the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention.

What is claimed is:

1. A method for introducing and withdrawing fluids from a patient comprising the steps of:

inserting a luer to a first position in a secondary conduit of a medical connector, said medical connector having a primary conduit with a primary fluid flowing therethrough, a secondary conduit and a hollow, resilient valve such that said primary fluid flows through said valve when said valve is in a decompressed state and wherein said primary fluid is prevented from flowing through said valve when said valve is in a compressed state;

forcing a second fluid contained in said luer into said secondary conduit thereby slightly deforming said valve such that both said primary and secondary fluids may travel through said medical connector to a patient simultaneously;

inserting said luer to a second position in said secondary conduit such that said primary fluid may not transverse said valve while fluid communication is established between said luer and the patient;

withdrawing fluid from said patient through said primary and secondary conduits and into said luer; and removing said luer thereby reestablishing said flow of said primary fluid from the source thereof through said medical connector to the patient.

2. The method of claim 1, wherein said withdrawing step is conducted after said inserting said luer to a second position step.

3. The method of claim 1, wherein said inserting a luer to a first position is conducted before said inserting a luer to a second position step.

4. The method of claim 1, wherein said inserting a luer to a second position is conducted before said inserting a luer to a first position step.

5. The method of claim 1, wherein said withdrawal step is conducted before said forcing step.

6. The method of claim 1, wherein said forcing step is conducted before said withdrawal step.

* * * * *